United States Patent
Gekkieva et al.

(10) Patent No.: US 10,035,850 B2
(45) Date of Patent: Jul. 31, 2018

(54) METHODS FOR TREATING NEOVASCULAR AGE-RELATED MACULAR DEGENERATION

(71) Applicant: Novartis AG, Basel (CH)

(72) Inventors: Margarita Gekkieva, Basel (CH);
Peter Sallstig, Fort Worth, TX (US);
Werner Schmidt, Fort Worth, TX (US);
James Warburton, Basel (CH);
Andreas Weichselberger, Basel (CH)

(73) Assignee: Novartis Pharma AG, Basel (CH)

(*) Notice: Subject to any disclaimer, the term of this patent is extended or adjusted under 35 U.S.C. 154(b) by 0 days.

(21) Appl. No.: 14/934,731

(22) Filed: Nov. 6, 2015

(65) Prior Publication Data

US 2016/0130337 A1    May 12, 2016

Related U.S. Application Data

(60) Provisional application No. 62/076,770, filed on Nov. 7, 2014, provisional application No. 62/088,061, filed on Dec. 5, 2014.

(51) Int. Cl.
| | |
|---|---|
| *C07K 16/22* | (2006.01) |
| *A61B 3/12* | (2006.01) |
| *A61K 39/395* | (2006.01) |
| *A61K 9/00* | (2006.01) |
| *A61B 5/00* | (2006.01) |
| *A61K 39/00* | (2006.01) |

(52) U.S. Cl.
CPC ........... *C07K 16/22* (2013.01); *A61B 3/12* (2013.01); *A61B 5/4848* (2013.01); *A61K 9/0048* (2013.01); *A61K 39/3955* (2013.01); *A61K 2039/54* (2013.01); *A61K 2039/545* (2013.01); *C07K 2317/24* (2013.01); *C07K 2317/52* (2013.01); *C07K 2317/522* (2013.01); *C07K 2317/56* (2013.01); *C07K 2317/565* (2013.01); *C07K 2317/567* (2013.01); *C07K 2317/569* (2013.01); *C07K 2317/622* (2013.01); *C07K 2317/76* (2013.01); *C07K 2317/94* (2013.01)

(58) Field of Classification Search
None
See application file for complete search history.

(56) References Cited

U.S. PATENT DOCUMENTS 8,349,322 B2 * 1/2013 Borras ................... C07K 16/22
424/130.1

FOREIGN PATENT DOCUMENTS

| EP | 2311433 | * | 4/2011 | ............ A61K 9/00 |
| WO | WO2012097019 | * | 7/2012 | ............ A61K 38/18 |
| WO | WO2015086830 | * | 6/2015 | ............ A61K 39/00 |

OTHER PUBLICATIONS

Alcon Research clinical trial (NCT01849692).*
Dugel P., Results of ESB 1008, a Single-Chain Antibody Fragment, for the Treatment of Neovascular AMD http://eyetube.net/series/dailycoverage-san-diego-august-2014/asile/.*
Anonymus—Brolucizumab (available on the internet at http://drugspider.com/drug/brolucizumab, retrieved on Nov. 7, 2016).*
I. Mantel et al., "Reducing the clinical burden of ranibizumab treatment for neovascular age-related macular degeneration using an individually planned regimen", British journal of ophthalmology, 98, 1192-1196, 2014.*
Tolentino et al. "Drugs in Phase II clinical trials for the treatment of age-related macular degeneration", Expert Opinion on Investigational Drugs, 24, 183-199, 2014.*
Anonymous, "Monthly and as-needed treatment in the SHORE study resulted in similar visual acuity gains in RVO" (Retina today, Sep. 1, 2014, pp. 14-17.*
Heier JS: Intravitreal Aflibercept for AMD: 2-year Results, Retina Today, Mar. 1, 2012, pp. 49-51.*

* cited by examiner

*Primary Examiner* — Elly-Gerald Stoica
(74) *Attorney, Agent, or Firm* — Jason J. Derry

(57) ABSTRACT

A method is provided for reducing the treatment burden for patients who have an intraocular neovascular disorder, the method comprising administering a therapeutically effective amount of VEGF antagonist on a dosing schedule that includes treatment intervals of 8 and/or 12 weeks.

10 Claims, 1 Drawing Sheet

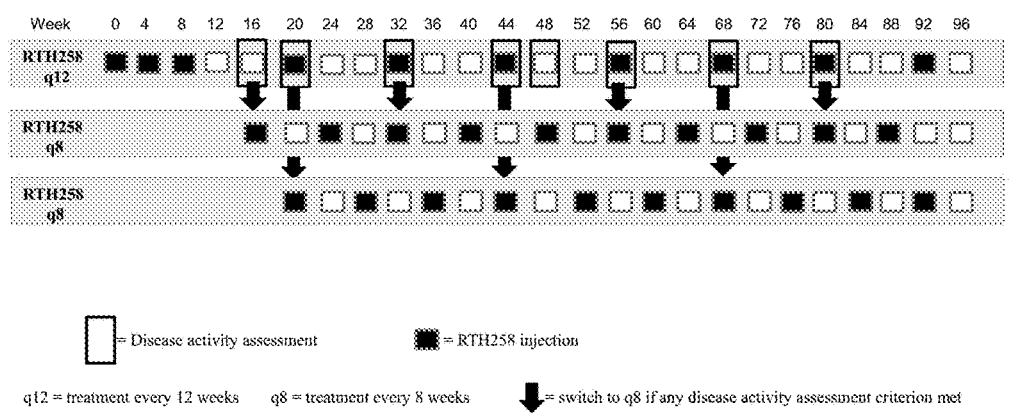

SEQUENCE LISTING

<160> NUMBER OF SEQ ID NOS: 3

<210> SEQ ID NO 1
<211> LENGTH: 120
<212> TYPE: PRT
<213> ORGANISM: Artificial Sequence
<220> FEATURE:
<223> OTHER INFORMATION: Synthetic heavy chain

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Asp His Asn Ser Gly Trp Gly Leu Asp Ile Trp Gly Gln
            100                 105                 110

Gly Thr Leu Val Thr Val Ser Ser
        115                 120
```

<210> SEQ ID NO 2
<211> LENGTH: 111
<212> TYPE: PRT
<213> ORGANISM: Artificial Sequence
<220> FEATURE:
<223> OTHER INFORMATION: Synthetic light chain

<400> SEQUENCE: 2

```
Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly
            100                 105                 110
```

<210> SEQ ID NO 3
<211> LENGTH: 251
<212> TYPE: PRT
<213> ORGANISM: Artificial Sequence
<220> FEATURE:
<223> OTHER INFORMATION: Synthetic antibody construct

<400> SEQUENCE: 3

```
Glu Ile Val Met Thr Gln Ser Pro Ser Thr Leu Ser Ala Ser Val Gly
1               5                   10                  15
```

```
Asp Arg Val Ile Ile Thr Cys Gln Ala Ser Glu Ile Ile His Ser Trp
            20              25              30

Leu Ala Trp Tyr Gln Gln Lys Pro Gly Lys Ala Pro Lys Leu Leu Ile
            35              40              45

Tyr Leu Ala Ser Thr Leu Ala Ser Gly Val Pro Ser Arg Phe Ser Gly
            50              55              60

Ser Gly Ser Gly Ala Glu Phe Thr Leu Thr Ile Ser Ser Leu Gln Pro
65              70              75              80

Asp Asp Phe Ala Thr Tyr Tyr Cys Gln Asn Val Tyr Leu Ala Ser Thr
            85              90              95

Asn Gly Ala Asn Phe Gly Gln Gly Thr Lys Leu Thr Val Leu Gly Gly
            100             105             110

Gly Gly Gly Ser Gly Gly Gly Gly Ser Gly Gly Gly Gly Ser Gly Gly
            115             120             125

Gly Gly Ser Glu Val Gln Leu Val Glu Ser Gly Gly Gly Leu Val Gln
            130             135             140

Pro Gly Gly Ser Leu Arg Leu Ser Cys Thr Ala Ser Gly Phe Ser Leu
145             150             155             160

Thr Asp Tyr Tyr Tyr Met Thr Trp Val Arg Gln Ala Pro Gly Lys Gly
            165             170             175

Leu Glu Trp Val Gly Phe Ile Asp Pro Asp Asp Pro Tyr Tyr Ala
            180             185             190

Thr Trp Ala Lys Gly Arg Phe Thr Ile Ser Arg Asp Asn Ser Lys Asn
            195             200             205

Thr Leu Tyr Leu Gln Met Asn Ser Leu Arg Ala Glu Asp Thr Ala Val
            210             215             220

Tyr Tyr Cys Ala Gly Gly Asp His Asn Ser Gly Trp Gly Leu Asp Ile
225             230             235             240

Trp Gly Gln Gly Thr Leu Val Thr Val Ser Ser
            245             250
```

METHODS FOR TREATING NEOVASCULAR AGE-RELATED MACULAR DEGENERATION

The present application claims priority to U.S. Provisional Application Ser. No. 62/076,770, filed on Nov. 7, 2014, and to U.S. Provisional Application Ser. No. 62/088,061, filed on Dec. 5, 2014, the disclosures of which are specifically incorporated by reference herein.

FIELD OF THE INVENTION

The invention relates to methods for treating an ocular disease with a VEGF antagonist. In particular, the invention relates to treating ocular neovascular disease with less frequent dosing than currently approved treatment regimens. Provided are methods for identifying patients that can be treated with a VEGF antagonist on an 8-week or 12-week dosing regimen, the patients having received a loading phase of three individual doses administered at 4-week intervals.

BACKGROUND OF THE INVENTION

Age-related macular degeneration (AMD) is the leading cause of severe vision loss in people affecting 10%-13% of individuals over the age of 65 in North America, Europe, and Australia (Kawasaki 2010, Rein et al., Arch Ophthalmol. 2009; 127:533-40, Smith 2001). Genetic, environmental and health factors play an important role in the pathogenesis of the disease.

AMD is classified into 2 clinical subtypes: the non-neovascular (atrophic) or dry form and the neovascular (exudative) or wet form (Ferris et al., Arch Ophthalmol. 1984; 102:1640-2, Lim et al., Lancet. 2012; 379:1728-38, Miller et al., Am J Ophthalmol. 2013; 155:1-35). Neovascular AMD (nAMD) is characterized by the growth of abnormal new blood vessels (neovascularization) under the RPE or subretinal space from the subjacent choroid, termed choroidal neovascularization (CNV) (Ferris et al., Arch Ophthalmol. 1984; 102:1640-2). These newly formed vessels have an increased likelihood to leak blood and serum, damaging the retina by stimulating inflammation and scar tissue formation. This damage to the retina results in progressive, severe, and irreversible vision loss (Shah et al., Am J Ophthalmol. 2007; 143:83-89, Shah et al., Am J Ophthalmol. 2009; 116:1901-07). Without treatment, most affected eyes will have poor central vision (20/200) within 12 months (TAP 2003). Although the neovascular form of the disease is only present in about 10% of all AMD cases, it accounted for approximately 90% of the severe vision loss from AMD prior to the introduction of anti-vascular endothelial growth factor (VEGF) treatments (Ferris et al., Am J Ophthalmol. 1983; 118:132-51, Sommer et al., N Engl J Med. 1991; 14:1412-17, Wong et al., Ophthalmology. 2008; 115:116-26).

VEGF has been shown to be elevated in patients with nAMD and is thought to play a key role in the neovascularization process (Spilsbury et al., Am J Pathol. 2000; 157:135-44). The use of intravitreal (IVT) pharmacotherapy targeting VEGF has significantly improved visual outcomes in patients with nAMD (Bloch et al., Am J Ophthalmol. 2012; 153:209-13, Campbell et al., Arch Ophthalmol. 2012; 130:794-5). Anti-VEGF treatments, such as ranibizumab (LUCENTIS®) and aflibercept (EYLEA®), inhibit VEGF signaling pathways and have been shown to halt the growth of neovascular lesions and resolve retinal edema.

In two Phase 3 studies of ranibizumab, with monthly dosing regimens, approximately 95% of ranibizumab treated subjects experienced stabilization of vision (defined as a loss of fewer than 15 ETDRS letters) or improvement in vision at 12 months compared with 62% and 64% in the control groups (Rosenfeld et al., N Engl J Med. 2006; 355:1419-31, Brown et al., N Engl J Med. 2006; 355:1432-44). Twenty-five to 40% of subjects in the ranibizumab groups gained ≥15 letters at 12 months compared with 5-6% in the 2 control groups. On average, ranibizumab treated subjects gained 7-11 letters of vision after 12 months, whereas control subjects lost an average of approximately 10 letters. This gain in visual acuity was essentially maintained during the second year of both Phase 3 studies while vision, on average, continued to decline in the control group. The visual acuity benefits, which indicate a suspension of nAMD rather than a slowdown of its progression, were supported by corresponding effects on lesion anatomy and subject reported outcomes. The latter demonstrated statistically and clinically meaningful improvements in near activities, distance activities, and vision specific dependency as measured by the National Eye Institute Visual Functioning Questionnaire—25 (VFQ-25).

In two parallel Phase 3 trials of aflibercept, treatment naïve subjects with nAMD were randomized to 2 doses (0.5 and 2.0 mg) and 2 regimen (every 4 weeks and every 8 weeks with 2.0 mg) or the control arm (ranibizumab 0.5 mg every 4 weeks). At 52 weeks, all aflibercept groups, independent of doses and regimen, were noninferior to the ranibizumab group with equal maintenance of vision in 95% of eyes (Heier et al., Ophthalmology. 2012; 119:2537-48). In the 2 mg aflibercept every 4 weeks group, there was a mean BCVA improvement of 9.3 letters and in the 2 mg aflibercept every 8 weeks group there was an improvement of 8.4 letters compared to the control group which had a mean improvement of 8.7 letters. In the second year of the study subjects were switched to a capped pro-re-nata (PRN) regimen. The proportion of subjects who maintained BCVA ranged between 91% and 92% for all groups. Mean BCVA improvements ranged from 7.9 (ranibizumab 0.5 mg every 4 weeks), 7.6 (aflibercept 2 mg every 4 weeks and every 8 weeks) to 6.6 (aflibercept 0.5 mg). Over all groups, a mean loss of 0.8-1.7 letters was seen after switching from a fixed to a capped PRN regimen. The retreatment frequency was similar between aflibercept and ranibizumab arms during the capped PRN year, with 4.1 injections for the aflibercept 2 mg every 4 weeks arm, 4.2 injections for the aflibercept 2 mg every 8 weeks arm and 4.7 for the ranibizumab 0.5 mg every 4 weeks arm (Schmidt-Erfurth et al., Br J Ophthalmol 2014; 98:1144-1167 2014; 98:1144-1167).

Monthly treatment or treatment every 2 months poses significant burden not only for the generally older patients but also for their caregivers and physicians. Also, although the treatments have proven to have a positive benefit/risk ratio, they are not without risk. Each injection carries with it the possibility of pain, sub-conjunctival hemorrhage, vitreous hemorrhage, retinal tear, retinal detachment, iatrogenic cataract, and endophthalmitis (Ohr et al., Expert Opin. Pharmacother. 2012; 13:585-591), as well as a sustained rise in intraocular pressure (IOP) with serial injections of anti-VEGF agents (Tseng et al., J Glaucoma. 2012; 21:241-47). Additionally, even with monthly IVT injections, 60-70% of patients gain less than 15 letters of visual acuity. Clearly there is a medical need to develop a product that, compared to the currently available products, achieves a greater gain in visual acuity in a higher number of patients and/or has a prolonged therapeutic effect.

SUMMARY OF THE INVENTION

The invention provides an improved method of administering a therapeutic VEGF antagonist for treating ocular diseases, in particular ocular neovascular diseases. In certain aspects, the invention provides methods for treating ocular neovascular disease comprising administering to a mammal three individual doses of a VEGF antagonist at 4-week (i.e., monthly) intervals, followed by additional doses every 12 weeks (q12) and/or every 8 weeks (q8) depending on the outcome of disease activity assessments using pre-defined visual and anatomic criteria.

In certain aspects, the VEGF antagonist used in a method of the invention is an anti-VEGF antibody. In a particular aspect, the anti-VEGF antibody is a single chain antibody (scFv) or Fab fragment. In particular, the anti-VEGF antibody is RTH258.

Specific preferred embodiments of the invention will become evident from the following more detailed description of certain preferred embodiments and the claims.

BRIEF DESCRIPTION OF THE FIGURES

FIG. 1 represents a dosing schedule for treating nAMD with RTH258.

DETAILED DESCRIPTION

Definitions

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of skill in the art, such as the Oxford Dictionary of Biochemistry and Molecular Biology (Ed. Anthony Smith, Oxford University Press, Oxford, 2004).

As used herein, all percentages are percentages by weight, unless stated otherwise.

As used herein and unless otherwise indicated, the terms "a" and "an" are taken to mean "one", "at least one" or "one or more". Unless otherwise required by context, singular terms used herein shall include pluralities and plural terms shall include the singular.

The contents of any patents, patent applications, and references cited throughout this specification are hereby incorporated by reference in their entireties.

The term "VEGF" refers to the 165-amino acid vascular endothelial cell growth factor, and related 121-, 189-, and 206-amino acid vascular endothelial cell growth factors, as described by Leung et al., Science 246:1306 (1989), and Houck et al., Mol. Endocrin. 5:1806 (1991) together with the naturally occurring allelic and processed forms of those growth factors.

The term "VEGF receptor" or "VEGFr" refers to a cellular receptor for VEGF, ordinarily a cell-surface receptor found on vascular endothelial cells, as well as variants thereof which retain the ability to bind hVEGF. One example of a VEGF receptor is the fms-like tyrosine kinase (flt), a transmembrane receptor in the tyrosine kinase family. DeVries et al., Science 255:989 (1992); Shibuya et al., Oncogene 5:519 (1990). The flt receptor comprises an extracellular domain, a transmembrane domain, and an intracellular domain with tyrosine kinase activity. The extracellular domain is involved in the binding of VEGF, whereas the intracellular domain is involved in signal transduction. Another example of a VEGF receptor is the flk-1 receptor (also referred to as KDR). Matthews et al., Proc. Nat. Acad. Sci. 88:9026 (1991); Terman et al., Oncogene 6:1677 (1991); Terman et al., Biochem. Biophys. Res. Commun. 187:1579 (1992). Binding of VEGF to the flt receptor results in the formation of at least two high molecular weight complexes, having an apparent molecular weight of 205,000 and 300,000 Daltons. The 300,000 Dalton complex is believed to be a dimer comprising two receptor molecules bound to a single molecule of VEGF.

As used herein, a "VEGF antagonist" refers to a compound that can diminish or inhibit VEGF activity in vivo. A VEGF antagonist can bind to a VEGF receptor(s) or block VEGF protein(s) from binding to VEGF receptor(s). A VEGF antagonist can be, for example, a small molecule, an anti-VEGF antibody or antigen-binding fragments thereof, fusion protein (such as aflibercept), an aptamer, an antisense nucleic acid molecule, an interfering RNA, receptor proteins, and the like that can bind specifically to one or more VEGF proteins or one or more VEGF receptors. Several VEGF antagonists are described in WO 2006/047325.

In a preferred embodiment, the VEGF antagonist is an anti-VEGF antibody.

The term "antibody" as used herein includes whole antibodies and any antigen binding fragment (i.e., "antigen-binding portion," "antigen binding polypeptide," or "immunobinder") or single chain thereof. An "antibody" includes a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion") refers to one or more fragments of an antibody that retain the ability to specifically bind to an antigen (e.g., VEGF). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a single domain or dAb fragment (Ward et al., (1989) Nature 341: 544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins. Antibodies can be of different isotype, for example, an IgG (e.g., an IgG1, IgG2, IgG3, or IgG4 subtype), IgA1, IgA2, IgD, IgE, or IgM antibody.

As used herein, a "mammal" includes any animal classified as a mammal, including, but not limited to, humans, domestic animals, farm animals, and companion animals, etc.

As used herein, the term "subject" or "patient" refers to human and non-human mammals, including but, not limited to, primates, rabbits, pigs, horses, dogs, cats, sheep, and cows. Preferably, a subject or patient is a human.

An "ocular disease" or "neovascular ocular disease" that can be treated using a method of the invention includes, a condition, disease, or disorder associated with ocular neovascularization, including, but not limited to, abnormal angiogenesis, choroidal neovascularization (CNV), retinal vascular permeability, retinal edema, diabetic retinopathy (particularly proliferative diabetic retinopathy), diabetic macular edema, neovascular (exudative) age-related macular degeneration (AMD), including CNV associated with nAMD (neovascular AMD), sequela associated with retinal ischemia, Central Retinal Vein Occlusion (CRVO), and posterior segment neovascularization.

Selection of Treatment Regimen

The invention provides methods for determining whether patients being treated with a VEGF antagonist for an ocular disease can be treated every eight weeks or every twelve weeks.

The invention provides methods for treating ocular neovascular diseases in a mammal, including neovascular age-related macular degeneration (nAMD), the methods comprising administering multiple doses of a VEGF antagonist to the mammal at various intervals for at least two years. In certain embodiments, the doses are administered at 4-week intervals for a total of 3 doses, followed by administering additional doses at 8-week, 12-week, or a combination of 8- and 12-week intervals. The invention provides specific criteria established by the inventors based on disease activity assessments to determine when an 8-week interval should be used and when a 12-week interval should be used. The invention further provides methods for determining when the treatment interval should be switched to the other treatment interval. For example, when a patient is selected for receiving doses at 12-week intervals (after an initial 3 dose loading phase as described herein), methods of the invention can be used to determine if a patient should continue on the 12-week interval regimen or switch to 8-week interval regimen, and methods of the invention can be used to determine if a patient should continue on the 8-week interval regimen or switch to the 12-week interval regimen. In some cases, a patient might be on a 12-week interval regimen for some time, and then switch to an 8-week interval, and then switch back to the 12-week interval. Thus, patients may not stay on one interval regimen, and may go back and forth depending on assessments according to the criteria set forth herein.

In one embodiment, the invention provides a method for treating ocular diseases, in particular, ocular neovascular diseases, comprising administering a VEGF antagonist to a mammal in need thereof according to the following schedule:

a "loading phase" of 3 doses administered at 4-week intervals (e.g., week 0, week 4, week 8), and additional doses at 8-week (q8) and/or 12-week (q12) intervals depending on selection criteria further described herein.

Disease activity assessments are conducted, for example, at Weeks 16, 20, 32 and 44 following initial injection of a VEGF antagonist, allowing four time points up to the end of the first year of treatment (Week 48) where q12 subjects, in certain embodiments, can be reassigned to q8 treatment. It is expected that early determination of subjects who are more suited to a q8 dosing regimen at Week 16 will minimize the percentage of q12 subjects who will require reassignment at later time points (reassignment is also permitted at Weeks 20, 32 or 44). Analyses from the PIER and EXCITE studies have shown that visual and anatomic response during and immediately after the loading phase are associated with visual acuity outcomes over the remainder of the first year of treatment. Recent analyses from the EXCITE study have also shown that subjects who lose vision during the initial loading phase will have better visual outcomes with more frequent treatment versus q12 treatment. Recent analyses from CATT and EXCITE have shown that new intra-retinal fluid/cysts, and to a lesser degree CSFT increase, are associated with visual acuity decline. These dynamic criteria support their use at the Week 16 disease activity assessment.

In one embodiment, patients treated with the initial 3 doses of a VEGF antagonist, are assessed at Weeks 12, 16, 20, 32, and 44 to determine if they should receive further doses at 8-week intervals or 12-week intervals.

In another embodiment, patients treated with the initial 3 doses of a VEGF antagonist, are assessed in a second year of treatment at Weeks 48, 56, 68, and 80 to determine if they should receive further doses at 8-week intervals or 12-week intervals.

At assessment weeks, the patients can be currently on an 8-week or 12-week interval regimen. Thus, the assessment can determine if a patient stays on the current interval or switches to the other interval.

An assessment as described herein includes determining the best-corrected visual acuity (BCVA), visual acuity (VA), central subfield thickness (CSFT) as measured by SD-OCT, and/or the presence of new or worsening intraretinal cysts/intraretinal fluid (IRC/IRF).

Means of determining and monitoring VA, BCVA, CSFT, and IRC/IRF are well understood and commonly used by those skilled in the art. For instance, a patient's visual performance can be monitored assessing changes in the number of letters the patient the mean change in the (BCVA) from baseline to a desired time. The baseline can be, for example, VA at the start of a therapeutic treatment or at a specified time point after treatment has started.

In certain embodiments, methods of the invention comprise determining the mean change in the BCVA from baseline to a specified time (e.g., Week 12 to Week 16), and assessing whether a subject loses fewer than a certain number of letters in visual acuity at a specified time compared with baseline (e.g., Week 12 to Week 16).

In certain embodiments, the selection criteria for determining if a patient should be treated every 8 weeks or every 12 weeks following the initial 3 doses given at 4-week intervals is as follows:

Week 0 Through Week 48

If met, the patients are assigned to receive injections of a VEGF antagonist every 8 weeks (q8) up to Week 48.

At Week 16:
Decrease in BCVA of ≥5 letters, due to neovascular AMD (nAMD) disease activity, at Week 16 compared to Baseline.
Decrease in BCVA of ≥5 letters, due to nAMD disease activity, at Week 16 compared to Week 12.
VA decline of ≥3 letters and CSFT increase ≥75 μm, at Week 16 compared to Week 12.
New or worsening intraretinal cysts (IRC)/intraretinal fluid (IRF) at Week 16 compared to Week 12.

At Week 20, 32 and 44:
Decrease in BCVA of ≥5 letters, due to nAMD disease activity, compared to Week 12.

In other embodiments, a method of the invention includes additional assessments after week 48 of the start of treatment as follows:

Week 48 Through Week 96

Patients assigned to q8 treatment at Weeks 16 and 20 are reassigned to a q12 treatment regimen for the second year of treatment if they do not meet any of the following criteria:

At Week 48:
Decrease in BCVA of ≥5 letters, due to nAMD disease activity, at Week 48 compared to Week 32.
New or worsening IRC/IRF at Week 48 compared to Week 32.

Subjects entering the second year of treatment on a q12 treatment regimen are maintained on a q12 regimen unless they meet the following criterion at any of the following visits:

At Week 56, 68 and 80:
Decrease in BCVA by ≥5 letters, due to nAMD disease activity, compared to Week 48.

Anti-VEGF Antibodies

In certain embodiments, a VEGF antagonist used in a method of the invention is an anti-VEGF antibody, particularly anti-VEGF antibodies described in WO 2009/155724, the entire contents of which are hereby incorporated by reference.

In one embodiment, the anti-VEGF antibody of the invention comprises a variable heavy chain having the sequence as set forth in SEQ ID NO: 1 and a variable light chain having the sequence as set forth in SEQ ID NO: 2.

VH:                                              SEQ ID NO. 1
EVQLVESGGGLVQPGGSLRLSCTASGFSLTDYYYMTWVRQAPGKGLEWVG

FIDPDDDPYYATWAKGRFTISRDNSKNTLYLQMNSLRAEDTAVYYCAGGD

HNSGWGLDIWGQGTLVTVSS

VL:                                              SEQ ID NO. 2
EIVMTQSPSTLSASVGDRVIITCQASEIIHSWLAWYQQKPGKAPKLLIYL

ASTLASGVPSRFSGSGSGAEFTLTISSLQPDDFATYYCQNVYLASTNGAN

FGQGTKLTVLG

In another embodiment, the anti-VEGF antibody used in a method of the invention comprises the sequence as set forth in SEQ ID NO: 3.

EIVMTQSPSTLSASVGDRVIITCQASEIIHSWLAWYQQKPGKAPKLLIYL

ASTLASGVPSRFSGSGSGAEFTLTISSLQPDDFATYYCQNVYLASTNGAN

FGQGTKLTVLGGGGSGGGGSGGGGSGGGGSEVQLVESGGGLVQPGGSLR

LSCTASGFSLTDYYYMTWVRQAPGKGLEWVGFIDPDDDPYYATWAKGRFT

ISRDNSKNTLYLQMNSLRAEDTAVYYCAGGDHNSGWGLDIWGQGTLVTVS

S

In a preferred embodiment, the anti-VEGF antibody used in a method of the invention is RTH258 (which comprises SEQ ID NO: 3). RTH258 is a humanized single-chain Fv (scFv) antibody fragment inhibitor of VEGF with a molecular weight of ~26 kDa. It is an inhibitor of VEGF-A and works by binding to the receptor binding site of the VEGF-A molecule, thereby preventing the interaction of VEGF-A with its receptors VEGFR1 and VEGFR2 on the surface of endothelial cells. Increased levels of signaling through the VEGF pathway are associated with pathologic ocular angiogenesis and retinal edema. Inhibition of the VEGF pathway has been shown to inhibit the growth of neovascular lesions and resolve retinal edema in patients with nAMD.

Pharmaceutical Preparations

In one aspect the methods of the invention comprise the use of pharmaceutical formulations comprising anti-VEGF antibodies. The term "pharmaceutical formulation" refers to preparations which are in such form as to permit the biological activity of the antibody or antibody derivative to be unequivocally effective, and which contain no additional components which are toxic to the subjects to which the formulation would be administered. "Pharmaceutically acceptable" excipients (vehicles, additives) are those which can reasonably be administered to a subject mammal to provide an effective dose of the active ingredient employed.

A "stable" formulation is one in which an antibody or antibody derivative therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Preferably, the formulation is stable at room temperature (about 30° C.) or at 40° C. for at least 1 week and/or stable at about 2-8° C. for at least 3 months to 2 years. Furthermore, the formulation is preferably stable following freezing (to, e.g., −70° C.) and thawing of the formulation.

An antibody or antibody derivative "retains its physical stability" in a pharmaceutical formulation if it meets the defined release specifications for aggregation, degradation, precipitation and/or denaturation upon visual examination of color and/or clarity, or as measured by UV light scattering or by size exclusion chromatography, or other suitable art recognized methods.

An antibody or antibody derivative "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-offlight mass spectrometry (MALDI/TOF MS), for example. Other types of chemical alteration include charge alteration (e.g. occurring as a result of deamidation) which can be evaluated by ion-exchange chromatography, for example.

An antibody or antibody derivative "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example. Other "biological activity" assays for antibodies are elaborated herein below.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

A "polyol" is a substance with multiple hydroxyl groups, and includes sugars (reducing and non-reducing sugars), sugar alcohols and sugar acids. Preferred polyols herein have a molecular weight which is less than about 600 kD (e.g. in the range from about 120 to about 400 kD). A "reducing sugar" is one which contains a hemiacetal group that can reduce metal ions or react covalently with lysine and other amino groups in proteins and a "non-reducing sugar" is one which does not have these properties of a reducing sugar. Examples of reducing sugars are fructose, mannose, maltose, lactose, arabinose, xylose, ribose, rhamnose, galactose and glucose. Non-reducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. Where it is desired that the formulation is freeze-thaw stable, the polyol is preferably one which does not crystallize at freezing temperatures (e.g. −20° C.) such that it destabilizes the antibody in the formulation. Non-reducing sugars such as sucrose and trehalose are the preferred polyols herein, with trehalose being preferred over sucrose, because of the superior solution stability of trehalose.

As used herein, "buffer" refers to a buffered solution that resists changes in pH by the action of its acid-base conjugate components. The buffer of this invention has a pH in the range from about 4.5 to about 8.0; preferably from about 5.5 to about 7. Examples of buffers that will control the pH in this range include acetate (e.g. sodium acetate), succinate (such as sodium succinate), gluconate, histidine, citrate and other organic acid buffers. Where a freeze-thaw stable formulation is desired, the buffer is preferably not phosphate.

In a pharmacological sense, in the context of the present invention, a "therapeutically effective amount" of an antibody or antibody derivative refers to an amount effective in the prevention or treatment of a disorder for the treatment of which the antibody or antibody derivative is effective. A "disease/disorder" is any condition that would benefit from treatment with the antibody or antibody derivative. This includes chronic and acute disorders or diseases including those pathological conditions which predispose the mammal to the disorder in question.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

The pharmaceutical compositions used in present invention comprise a VEGF antagonist, preferably an anti-VEGF antibody, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

A carrier is a substance that may be associated with an antibody or antibody derivative prior to administration to a patient, often for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and polysaccharides such as aminodextran and polyamidoamines. Carriers also include solid support materials such as beads and microparticles comprising, for example, polylactate polyglycolate, poly(lactide-co-glycolide), polyacrylate, latex, starch, cellulose or dextran. A carrier may bear the compounds in a variety of ways, including covalent bonding (either directly or via a linker group), noncovalent interaction or admixture.

Pharmaceutical compositions may be formulated for any appropriate manner of administration, including, for example, topical, intraocular, oral, nasal, rectal or parenteral administration. In certain embodiments, compositions in a form suitable for intraocular injection, such as intravitreal injection, are preferred. Other forms include, for example, pills, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. The term parenteral as used herein includes subcutaneous, intradermal, intravascular (e.g., intravenous), intramuscular, spinal, intracranial, intrathecal and intraperitoneal injection, as well as any similar injection or infusion technique.

The pharmaceutical composition may be prepared as a sterile injectable aqueous or oleaginous suspension in which the active agent (i.e. VEGF antagonist), depending on the vehicle and concentration used, is either suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid may be used in the preparation of injectable compositions, and adjuvants such as local anesthetics, preservatives and/or buffering agents can be dissolved in the vehicle.

Dosage

A dose used in a method of the invention is based on the specific disease or condition being treated. The term "therapeutically effective dose" is defined as an amount sufficient to achieve or at least partially achieve the desired effect. A therapeutically effective dose is sufficient if it can produce even an incremental change in the symptoms or conditions associated with the disease. The therapeutically effective dose does not have to completely cure the disease or completely eliminate symptoms. Preferably, the therapeutically effective dose can at least partially arrest the disease and its complications in a patient already suffering from the disease. Amounts effective for this use will depend upon the severity of the disorder being treated and the general state of the patient's own immune system.

The dose amount can be readily determined using known dosage adjustment techniques by a physician having ordinary skill in treatment of the disease or condition. The therapeutically effective amount of a VEGF antagonist used in a method of the invention is determined by taking into account the desired dose volumes and mode(s) of administration, for example. Typically, therapeutically effective compositions are administered in a dosage ranging from 0.001 mg/ml to about 200 mg/ml per dose. Preferably, a dosage used in a method of the invention is about 60 mg/ml to about 120 mg/ml (i.e., about 60, 70, 80, 90, 100, 110, or 120 mg/ml). In a preferred embodiment, the dosage of an anti-VEGF antibody used in to method of the invention is 60 mg/ml or 120 mg/ml.

An aqueous formulation of an anti-VEGF antibody used in a method of the invention is prepared in a pH-buffered solution. Preferably, the buffer of such aqueous formulation has a pH in the range from about 4.5 to about 8.0, preferably from about 5.5 to about 7.0, most preferably about 6.75. Examples of buffers that will control the pH within this range include acetate (e.g. sodium acetate), succinate (such as sodium succinate), gluconate, histidine, citrate and other organic acid buffers. The buffer concentration can be from about 1 mM to about 50 mM, preferably from about 5 mM to about 30 mM, depending, for example, on the buffer and the desired isotonicity of the formulation.

A polyol, which acts as a tonicifier, may be used to stabilize an antibody in an aqueous formulation. In preferred embodiments, the polyol is a non-reducing sugar, such as sucrose or trehalose. If desired, the polyol is added to the formulation in an amount that may vary with respect to the desired isotonicity of the formulation. Preferably the aqueous formulation is isotonic, in which case suitable concentrations of the polyol in the formulation are in the range from about 1% to about 15% w/v, preferably in the range from about 2% to about 10% w/v, for example. However, hypertonic or hypotonic formulations may also be suitable. The amount of polyol added may also alter with respect to the molecular weight of the polyol. For example, a lower amount of a monosaccharide (e.g. mannitol) may be added, compared to a disaccharide (such as trehalose).

A surfactant is also added to an aqueous antibody formulation. Exemplary surfactants include nonionic surfactants such as polysorbates (e.g. polysorbates 20, 80 etc) or poloxamers (e.g. poloxamer 188). The amount of surfactant added is such that it reduces aggregation of the formulated antibody/antibody derivative and/or minimizes the formation of particulates in the formulation and/or reduces adsorption. For example, the surfactant may be present in the formulation in an amount from about 0.001% to about 0.5%, preferably from about 0.005% to about 0.2% and most preferably from about 0.01% to about 0.1%.

In one embodiment, an aqueous antibody formulation used in a method of the invention is essentially free of one or more preservatives, such as benzyl alcohol, phenol, m-cresol, chlorobutanol and benzethonium Cl. In another embodiment, a preservative may be included in the formulation, particularly where the formulation is a multidose formulation. The concentration of preservative may be in the range from about 0.1% to about 2%, most preferably from about 0.5% to about 1%. One or more other pharmaceutically acceptable carriers, excipients or stabilizers such as those described in Remington's Pharmaceutical Sciences 21st edition, Osol, A. Ed. (2006) may be included in the formulation provided that they do not adversely affect the desired characteristics of the formulation. Acceptable carriers, excipients or stabilizers are non-toxic to recipients at the dosages and concentrations employed and include: additional buffering agents, co-solvents, antioxidants including ascorbic acid and methionine, chelating agents such as EDTA, metal complexes (e.g. Zn-protein complexes), biodegradable polymers such as polyesters, and/or salt-forming counterions such as sodium.

Formulations to be used for in vivo administration must be sterile. This is readily accomplished by filtration through sterile filtration membranes, prior to, or following, preparation of the formulation.

In one embodiment, a VEGF antagonist is administered to an eye of a mammal in need of treatment in accordance with known methods for ocular delivery. Preferably, the mammal is a human, the VEGF antagonist is an anti-VEGF antibody, and the antibody is administered directly to an eye. Administration to a patient can be accomplished, for example, by intravitreal injection The VEGF antagonist in a method of the invention can be administered as the sole treatment or in conjunction with other drugs or therapies useful in treating the condition in question.

A preferred formulation for RTH258 for intravitreal injection is shown in the table below. Preferred concentrations of RTH258 are 6 mg/50 µL and 3 mg/50 µL.

TABLE 1

Preferred Aqueous Formulation

| Component | Concentration (W/V %) | Concentration Range (W/V %) |
|---|---|---|
| RTH258 | 12 | 6-12 |
| Citric Acid, anhydrous | 0.009 | 0.006-0.012 |
| Trisodium citrate (dihydrate) | 0.428 | 0.285-0.57 |
| Sucrose | 6.75 | 6.75 |
| Polysorbate 80 | 0.05% | 0.05% |
| Hydrochloric acid or Sodium hydroxide | pH 6.75 | pH 6.75 |
| Water for injection | qs 100 | qs 100 |

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The example below represents a preferred method of the invention over a two year treatment period. However, it shall be understood that variations of the following are within the scope of the invention and certain variations and other preferred embodiments are described herein. Further, it should be understood the treatment period may be longer than two years, and assessments can be done at the discretion of the physician or on the same schedule as described for the two year period (i.e., beginning of year three is considered week 0, and assessments are done at weeks counting from week 0, year 3).

EXAMPLES

Two treatment groups of subjects with untreated active CNV due to AMD receive multiple injections of RTH258. One group receives 3 mg/50 µL and the other group RTH258 6 mg/50 µL, initially injected 3 times at 4 week intervals (Day 0, Week 4 and Week 8), followed by injections (intravitreally) every 12 weeks (q12) during the first year (Week 48), unless the subject meets any of the criteria set forth below for Weeks 0 through 48 at any of the following visits. If the criteria are met, the subjects are assigned to receive injections every 8 weeks (q8) up to Week 48. Beginning at Week 16, at visits when subjects do not receive an active injection they are administered a sham injection. For the sham injection the tip of an injection syringe (the hub without a needle) is used. All doses are delivered in 50 µL (0.05 mL).

The study eye is assessed before, immediately (0-5 minutes) post-injection/sham, and 30 (±15) minutes after each injection/sham to ensure that the procedure and/or the study medication have not endangered the health of the eye.

Assessment of the study eye of all subjects is conducted at Visit 6/Week 16, Visit 7/Week 20, Visit 10/Week 32, Visit 13/Week 44, Visit 16/Week 56, Visit 19/Week 68 and Visit 22/Week 80. If the subject presents with new or worsening disease activity, as defined in the criteria specifically outlined below, the subject is reassigned to a q8 treatment regimen.

At Week 48, the subject study eye is assessed for absence of new or worsening disease activity. If the subject was switched to a q8 treatment at Week 16 or Week 20 and presents without new or worsening disease activity, as defined below, the subject is reassigned to a q12 treatment regimen.

Disease activity assessments are conducted at Weeks 16, 20, 32 and 44, allowing four time points up to the primary endpoint of the study (Week 48) where q12 subjects can be reassigned to q8 treatment. It is expected that early determination of subjects who are more suited to a q8 dosing regimen at Week 16 will minimize the percentage of q12 subjects who will require reassignment at later time points (reassignment is also permitted at Weeks 20, 32 or 44).

Early treatment diabetic retinopathy study (ETDRS) visual acuity testing is used prior to any examination requiring administration of eye drops to dilate the eye or any examination requiring contact with the eye. Visual acuity testing is performed following refraction and completed according to standard procedure.

Central subfield thickness (CSFT) is measured using SD-OCT.

The following criteria are used during the first year and second year to determine the dosing administration regimen for each subject in the study.

Day 0 Through Week 44

If the following criteria are met, the subjects initially injected 3 times at 4 week intervals (Day 0, Week 4 and Week 8), are assigned to receive injections every 8 weeks (q8) up to Week 48.

At Week 16:
Decrease in BCVA of ≥5 letters, due to neovascular AMD (nAMD) disease activity, at Week 16 compared to Baseline (as assessed at Day 0).
Decrease in BCVA of ≥5 letters, due to nAMD disease activity, at Week 16 compared to Week 12.
VA decline of ≥3 letters and CSFT increase ≥75 µm, at Week 16 compared to Week 12.
New or worsening intraretinal cysts (IRC)/intraretinal fluid (IRF) at Week 16 compared to Week 12.

At Week 20, 32 and 44:
Decrease in BCVA of ≥5 letters, due to nAMD disease activity, compared to Week 12.

Week 48 Through Week 96

Patients assigned to q8 treatment at Weeks 16 and 20 may be reassigned to a q12 treatment regimen for the second year of treatment if they do not meet any of the following criteria:

At Week 48:
Decrease in BCVA of ≥5 letters, due to nAMD disease activity, at Week 48 compared to Week 32.
New or worsening IRC/IRF at Week 48 compared to Week 32.

Patients entering the second year of treatment on a q12 treatment regimen will be maintained on a q12 regimen unless they meet the following criterion at any of the following visits:

At Week 56, 68 and 80:
Decrease in BCVA by ≥5 letters, due to nAMD disease activity, compared to Week 48.

Subjects are expected to have a beneficial change in BCVA from baseline at Week 48 and improved subject-reported outcomes over the study period, up to and including Week 96, while determining a beneficial, less frequent treatment regimen for certain subjects relative to current treatment regimens available for treatment of subjects having neovascular ocular disease.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein. The claims should not be read as limited to the described order or elements unless stated to that effect. It should be understood that various changes in form and detail may be made without departing from the scope of the appended claims.

What is claimed is:

1. A method for treating neovascular age-related macular degeneration (nAMD) in a mammal, the method comprising:
   a) administering to the mammal three individual doses of a VEGF antagonist at 4-week intervals, wherein the VEGF antagonist is an anti-VEGF antibody that comprises the sequence of SEQ ID NO: 3;
   b) assessing the mammal for best corrected visual acuity (BCVA), visual acuity (VA), central subfield thickness (CSFT), and the presence of intraretinal cysts/fluid at week 12;
   c) assessing the mammal for BCVA, VA, CSFT, and the presence of intraretinal cysts/fluid at week 16;
   d) assessing the mammal for BCVA, VA, CSFT, and the presence of intraretinal cysts/fluid at week 20; and
   e) administering to the mammal an additional dose of the VEGF antagonist at week 20 and once every 8 weeks (q8 regimen) thereafter if the following criteria are met and every 12 weeks (q12 regimen) thereafter if the following criteria are not met:
      a) decrease in BCVA of ≥5 letters, due to nAMD disease activity, at Week 16 compared to Baseline,
      b) decrease in BCVA of ≥5 letters, due to nAMD disease activity, at Week 16 compared to Week 12,
      c) VA decline of ≥3 letters and CSFT increase ≥75 μm, at Week 16 compared to Week 12, and
      d) new or worsening intraretinal cysts (IRC)/intraretinal fluid (IRF) at Week 16 compared to Week 12.

2. The method of claim 1, further comprising assessing the mammal at Weeks 32 and 44 for BCVA, and administering to the mammals additional doses on a q8 regimen after the further assessment at Week 32 or 44 if BCVA is ≥5 letters due to nAMD disease activity compared to Week 12.

3. The method of claim 1, wherein the mammal is a human.

4. The method of claim 1, wherein the VEGF antagonist is administered by intravitreal injection.

5. A method for treating neovascular AMD (nAMD) comprising administering to a mammal three individual doses of a VEGF antagonist at 4-week intervals, followed by additional doses every 12 weeks (q12) and/or every 8 weeks (q8) depending on the outcome of disease activity assessments using pre-defined visual and anatomic criteria as assessed at Weeks 12, 16, 20, 32, and 44 after the first individual dose is administered, wherein the VEGF antagonist is an anti-VEGF antibody that comprises the sequence of SEQ ID NO: 3, wherein the mammal is treated every 8 weeks (q8 regimen) starting at Week 16 if the following criteria are met and every 12 weeks (q12 regimen) starting at Week 20 if the following criteria are not met:
   a) decrease in BCVA of ≥5 letters, due to neovascular AMD (nAMD) disease activity, at Week 16 compared to Baseline, b) decrease in BCVA of ≥5 letters, due to nAMD disease activity, at Week 16 compared to Week 12, c) VA decline of ≥3 letters and CSFT increase ≥75 μm, at Week 16 compared to Week 12, and d) new or worsening intraretinal cysts (IRC)/intraretinal fluid (IRF) at Week 16 compared to Week 12.

6. The method of claim 5, further comprising assessing a mammal selected for q12 regimen at weeks 20, 32, and 44 for BCVA, and treating the mammals on a q8 regimen after the further assessment if BCVA is ≥5 letters due to nAMD disease activity compared to Week 12.

7. The method of claim 5, wherein the mammal is a human.

8. The method of claim 5, wherein the VEGF antagonist is administered by intravitreal injection.

9. The method of claim 5, wherein additional disease activity assessments are made at Weeks 48, 56, 68, and 80.

10. The method of claim 5, wherein the disease activity assessment comprises assessing BCVA, VA, central subfield thickness (CSFT), and/or presence of intraretinal cysts/fluid (IRC/IRF).

* * * * *